United States Patent
Woyewoda et al.

(10) Patent No.: US 9,068,139 B2
(45) Date of Patent: Jun. 30, 2015

(54) METHOD FOR EXTRACTING OIL FROM SEA CUCUMBER MATERIAL

(71) Applicants: Andrew Dennis Woyewoda, Dartmouth (CA); Elda C. Merlini, Lunenburg (CA); Jamie N. Russell, Lower Sackville (CA)

(72) Inventors: Andrew Dennis Woyewoda, Dartmouth (CA); Elda C. Merlini, Lunenburg (CA); Jamie N. Russell, Lower Sackville (CA)

(73) Assignee: Ocean Leader Fisheries Limited (CA)

( * ) Notice: Subject to any disclaimer, the term of this patent is extended or adjusted under 35 U.S.C. 154(b) by 258 days.

(21) Appl. No.: 13/723,808

(22) Filed: Dec. 21, 2012

(65) Prior Publication Data

US 2014/0179939 A1   Jun. 26, 2014

(30) Foreign Application Priority Data

Oct. 25, 2012 (CA) .................................. 2793322

(51) Int. Cl.
*C11C 1/00* (2006.01)
*C11B 3/00* (2006.01)
*C11B 1/02* (2006.01)
*C11B 3/16* (2006.01)

(52) U.S. Cl.
CPC ............... *C11B 3/003* (2013.01); *C11B 1/025* (2013.01); *C11B 3/001* (2013.01); *C11B 3/16* (2013.01)

(58) Field of Classification Search
CPC .......... C11B 1/025; C11B 1/00; C11B 3/003; A23J 3/30; A23J 7/00
USPC ............................................... 435/271
See application file for complete search history.

(56) References Cited

U.S. PATENT DOCUMENTS

| 6,055,936 A | 5/2000 | Collin |
| 6,399,105 B1 * | 6/2002 | Collin ........................ 424/550 |
| 6,685,975 B2 | 2/2004 | Saxby et al. |

OTHER PUBLICATIONS

"Fish Protein Hydrolyzate," web page of GEA Westfalia Separator Group, http://www.westfalia- separator.com/applications/renewable-resources/fish-protein-hydrolyzate.html (at least as early as Jul. 15, 2012).

Chen and Myers, "Extraction of Astaxanthin Pigment from Crawfish Waste Using a Soy Oil Process," Journal of Food Science, vol. 47 pp. 892-896 (1982) (Abstract) see http://onlinelibrary.wiley.com/doi/10.1111/j.1365-2621.1982.tb12739.x/abstract.

Chen and Myers, "Ensilage Treatment of Crawfish Waste for Improvement of Astaxanthin Pigment Extraction," Journal of Food Science, vol. 48, pp. 1516-1520 (1983) (Abstract) see http://onlinelibrary.wiley.com/doi/10.1111/.1365-2621.1983.tb03528.x/abstract.

* cited by examiner

*Primary Examiner* — Deborah D Carr
(74) *Attorney, Agent, or Firm* — Thompson Hine LLP

(57) ABSTRACT

A method for extracting oil from sea cucumber material. The sea cucumber material is mixed with water and the mixture is heated at a predetermined heating temperature for a predetermined heating time interval. The pH value and temperature of the mixture are adjusted to be compatible with an enzyme. A predetermined amount of the enzyme is then added to the mixture. The mixture is incubated at a predetermined incubation temperature for a predetermined incubation time interval. After the incubation the oil is removed from the mixture.

18 Claims, 6 Drawing Sheets

US 9,068,139 B2

METHOD FOR EXTRACTING OIL FROM SEA CUCUMBER MATERIAL

This application claims priority to Canadian Patent Application No. 2793322, filed on Oct. 25, 2012, entitled METHOD FOR EXTRACTING OIL FROM SEA CUCUMBER MATERIAL in the name of Andrew Dennis Woyewoda, Elda Merlini and Jamie Russell as inventors and Ocean Leader Fisheries Limited as assignee. The entire contents of that application are incorporated by reference herein.

FIELD

The present invention relates to a method for extracting oil from sea cucumber material, and more particularly, to a method for extracting oil from sea cucumber material using an enzyme.

BACKGROUND

Sea cucumber is used in fresh or dried form in various cuisines. Most cultures in East and South East Asia consider sea cucumber a delicacy. Sea cucumber is also considered a valuable source of various substances that serve as natural health products and have the potential of being developed into pharmaceutical drugs.

There are several sea cucumber species in the North Atlantic and adjacent seas but only one, the orange-footed sea cucumber "*Cucumaria frondosa*" is currently harvested. It is one of the most abundant and widespread species of sea cucumber within the North Atlantic Ocean and the Barents Sea. During the harvesting of sea cucumber, waste materials such as the head and viscera of the sea cucumber—hereinafter referred to as the "sea cucumber waste materials"—contain oils, which if extracted from the sea cucumber waste materials are useful for dietary and medicinal purposes.

U.S. Pat. No. 6,399,105 to Collin describes a method to extract sea cucumber oil from sea cucumber visceral material using a standard solvent extraction. Solvent extraction is a very efficient method and results in a substantially complete oil extraction. However, solvent extraction, while simple in principle, is relatively complex in operation. Solvents like hexanes that boil at fairly low temperatures are used since they are readily removed.

Unfortunately, most of these solvents are dangerous to handle, and the operation must be carried out in explosion proof facilities with appropriate safeguards being used for storage, handling, venting, discharge and/or disposal of the solvent materials. While solvent extraction is currently the preferred method utilized by many large cooking oil manufacturers, it is not currently widely used by fish oil manufacturers or manufacturers of dietary supplements of healthy food ingredients.

It is desirable to provide a method for extracting oil from sea cucumber material using an enzyme.

It is also desirable to provide a compound comprising oil extracted from sea cucumber material using an enzyme.

SUMMARY

Accordingly, one object of the present invention is to provide a method for extracting oil from sea cucumber material using an enzyme.

Another object of the present invention is to provide a compound comprising oil extracted from sea cucumber material using an enzyme.

According to one aspect of the present invention, there is provided a method for extracting oil from sea cucumber material. The sea cucumber material is mixed with water and the mixture is heated at a predetermined heating temperature for a predetermined heating time interval. The pH value and temperature of the mixture are adjusted to be compatible with an enzyme. A predetermined amount of the enzyme is then added to the mixture. The mixture is incubated at a predetermined incubation temperature for a predetermined incubation time interval. After the incubation the oil is removed from the mixture.

According to one aspect of the present invention, there is further provided a method for extracting oil from sea cucumber material. The sea cucumber material is mixed with water and the mixture is heated at a predetermined heating temperature for a predetermined heating time interval. The pH value and temperature of the mixture are adjusted to be compatible with an enzyme. A predetermined amount of the enzyme is then added to the mixture. The mixture is incubated at a predetermined incubation temperature for a predetermined incubation time interval. After elapse of the predetermined incubation time interval the mixture is pasteurized and a predetermined amount of a plant or animal based oil is added to the pasteurized mixture. The mixture is then centrifuged and the oil layer is removed after centrifuging.

According to another aspect of the present invention, there is further provided a method for extracting oil from sea cucumber material. The sea cucumber material is mixed with water and the mixture is heated at a predetermined heating temperature for a predetermined heating time interval. The pH value and temperature of the mixture are adjusted to be compatible with an enzyme. A predetermined amount of the enzyme is then added to the mixture. The mixture is incubated at a predetermined incubation temperature for a predetermined incubation time interval. After elapse of the predetermined incubation time interval the mixture is pasteurized and a first predetermined amount of a plant or animal based oil is added to the pasteurized mixture. The mixture is then centrifuged and the oil layer is removed after centrifuging. A second predetermined amount of a plant or animal based oil is then added to the remaining mixture. The remaining mixture is then centrifuged and the oil layer is removed after centrifuging.

According to one aspect of the present invention, there is provided a compound comprising oil extracted from sea cucumber material using an enzyme.

One advantage of the present invention is that it provides a method for extracting oil from sea cucumber material using an enzyme.

A further advantage of the present invention is that it provides a compound comprising oil extracted from sea cucumber material using an enzyme.

BRIEF DESCRIPTION OF THE DRAWINGS

A certain embodiment of the present invention is described below with reference to the accompanying drawing, in which.

DETAILED DESCRIPTION

Figure 1A:
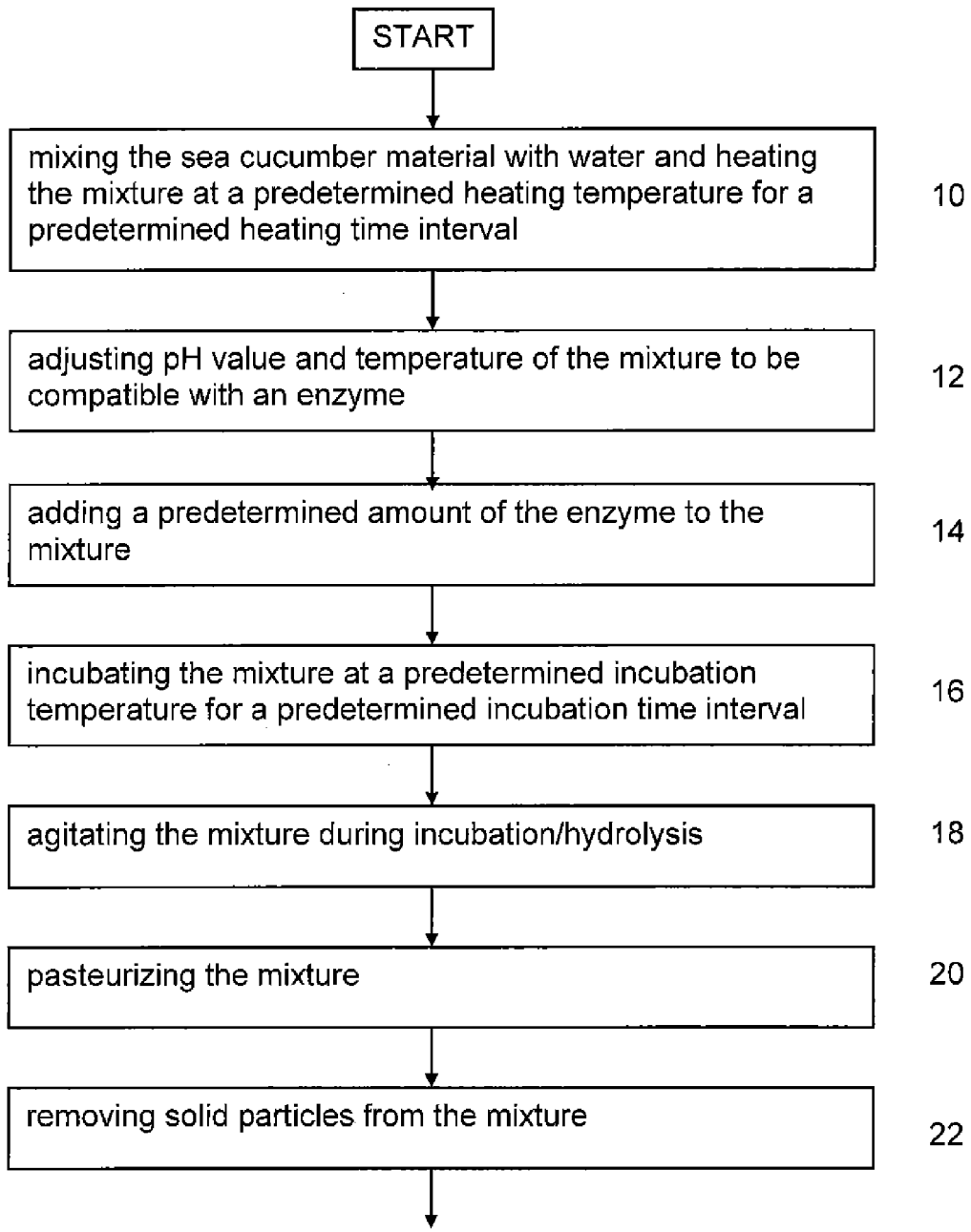
FIGS. 1*a* and 1*b* are simplified flow diagrams illustrating a method for extracting oil from sea cucumber material according to one embodiment of the invention; and, FIGS. 2*a* and 2*b* are simplified flow diagrams illustrating a method for extracting oil from sea cucumber material according to another embodiment of the invention.
Figure 1A:
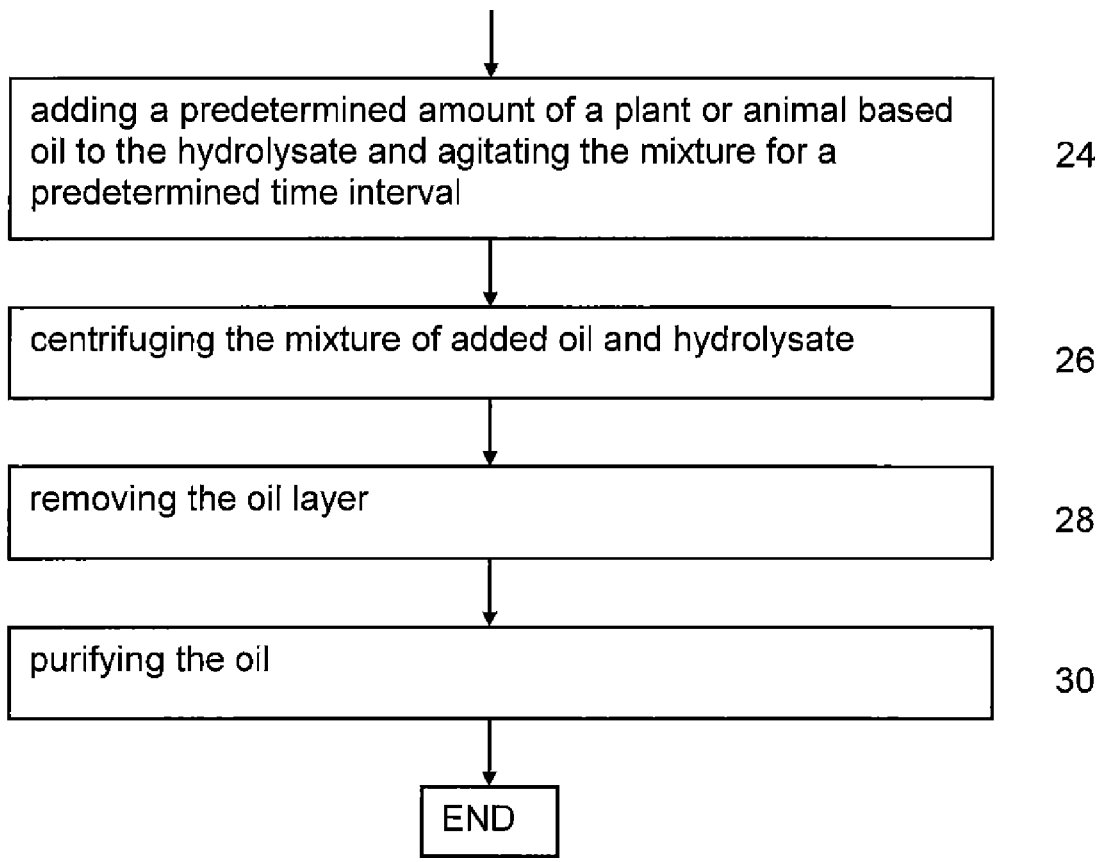

Unless defined otherwise, all technical and scientific terms used herein have the same meaning as commonly understood by one of ordinary skill in the art to which the invention belongs. Although any methods and materials similar or equivalent to those described herein can be used in the practice or testing of the present invention, certain methods and materials are now described.

While the description of certain embodiments herein below is with reference to sea cucumber waste materials of the species *Cucumaria frondosa*, it will become evident to those skilled in the art that the embodiments of the invention are not limited thereto, but are also applicable for extracting oil from waste materials of various other sea cucumber species, as well as other materials than waste materials. Of course one of skill in the art will use caution to use only species that provide oil absent poisonous/harmful substances, for example, by testing the extracted oil.

The sea cucumber may be harvested from the sea in a traditional manner with the freshly harvested sea cucumber being stored in a refrigerated location onboard the fishing vessel, in one case at approximately 4° C. to minimize the effect of microbial, chemical and enzymatic degradation of the sea cucumber tissue. The harvested sea cucumber is then transported, in one case at 4° C., to a processing plant for processing with the sea cucumber remaining in refrigerated storage in one case between 0° C. and 2° C. until commencement of the processing. During processing cutters remove one end of the sea cucumber, the carcass is split, and the viscera/guts, i.e. the waste material, are removed which are then washed with brine and/or freshwater and frozen at approximately −25° C. in, for example, 15-20 kg portions. For the oil extraction the frozen sea cucumber waste material is then prepared for provision in an unfrozen state.

In the method for extracting oil from sea cucumber material according to one embodiment of the invention described herein below enzymes, and particularly neutral or alkaline proteases, are utilized to separate the sea cucumber oil from sea cucumber material such as, for example:

1. *Bacillus subtilis* (CAS 76774-43-1, E.C.3.4.24.28) that can be recognized under various names, such as bacillolysin, procollagen C-terminal proteinase, carboxyprocollagen peptidase, procollagen C-terminal peptidase, procollagen C-proteinase, procollagen C-terminal proteinase, procollagen carboxypeptidase, procollagen carboxy-terminal proteinase, and procollagen peptidase which are commercially available from various suppliers under various names, such as, for example the name Amano N (available from Amano Enzyme Inc.) or Protex 40M/Protex 40L (industrial grade versions developed by Genecor). *Bacilus subtilis* is historically used for fermented production in Japan and is considered to be a safe microorganism;
2. Subtilisin. Alcalase 2.4 L FG (E.C. 3.4.21.62, Novozymes Ltd.) is a suitable subtilisin preparation from *Bacillus lichenformis*. It contains Subtilisin A (Subtilisin Carlsberg), an endoproteinase (MW~27, 300) of the serine type from *Bacillus licheniformis*. Protex 6L is a similar alkaline protease derived from *Bacillus licheniformis* and marketed by Genencor, it is alkaline serine endopeptidase of 22.5 KDa size; and,
3. Flavourzyme, a fungal protease-peptidase enzyme complex (E.C. 3.4.11.1). The complex exhibits both fungal protease-peptidase enzyme complex exopeptidase and endoproteinase activities.

Other proteases such as, for example: Acid Protease A (*Aspergillus niger*); Protease M "Amano" (*Aspergillus oryzae*); Protease NL "Amano" (*Bacillus subtilis*); Protease P "Amano" 6 (*Aspergillus melleus*); Protease S "Amano" (*Bacillus stearothermophilus*); Umamizyme (*Aspergillus oryzae*); Peptidase R (*Rhizopus oryzae*); Acid Protease DS; "Protease S "amino" G; Protizyme™; Alcalase®; Neutrase®); THERMOASE PC10F (*Bacillus stearothermophilus*); THERMOASE C160 (*Bacillus stearothermophilus*); PROTIN SD-AC10F (*Bacillus licheniformis*); PROTIN SD-AY10 (*Bacillus licheniformis*); PROTIN SD-PC10F (*Bacillus subtilis*); PROTIN SD-NY10 (*Bacillus subtilis*); Savinase 16L Type EX; Novozyme 37017; Ovozyme 48 BT; and similar proteases may also be utilized.

Figure 1B:
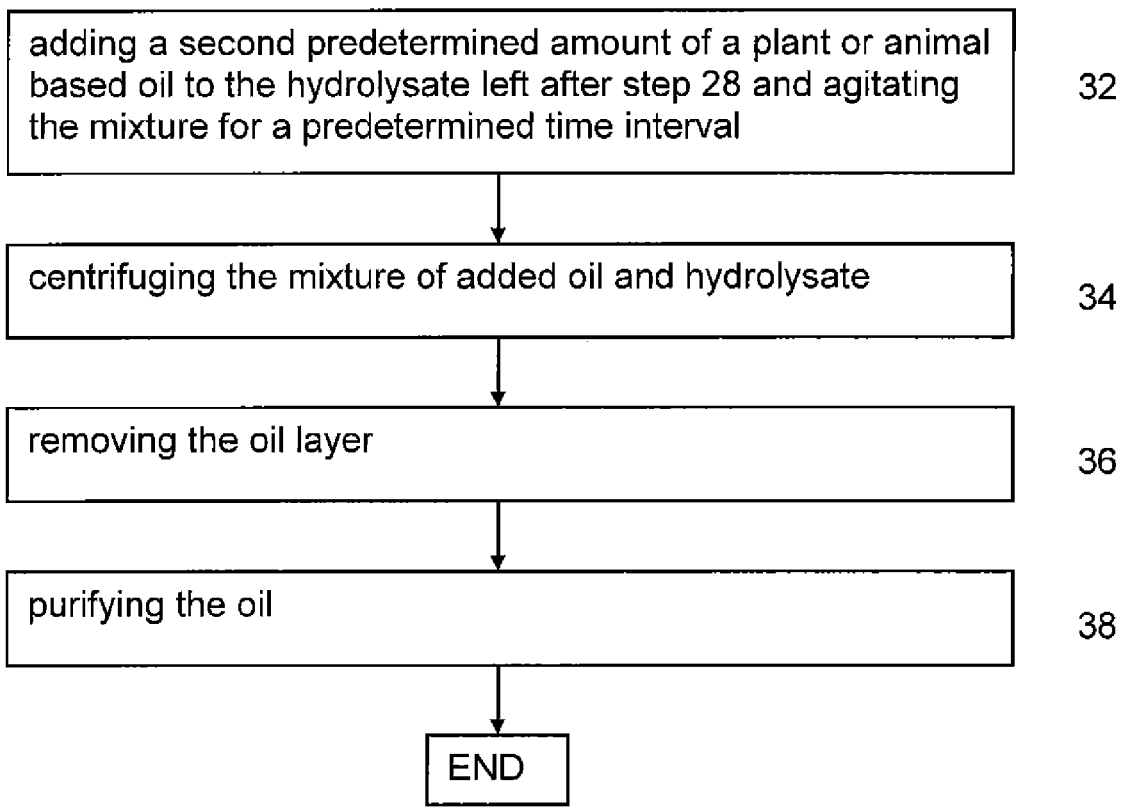

Referring to FIGS. 1*a* and 1*b*, a method for extracting oil from sea cucumber material according to a first embodiment of the invention is provided. At 10, the sea cucumber material—such as, ground sea cucumber viscera, i.e. waste material from processing—is mixed with water and the mixture is heated at a predetermined heating temperature for a predetermined heating time interval. It is noted that, in one case, the sea cucumber waste material does not include whole sea cucumbers such as, for example, inferior sea cucumbers discarded from the processing, since whole sea cucumbers have a low amount of oil.

The pH value and the temperature of the mixture are then adjusted—12—to be compatible with an enzyme, which will be added in a following step. At 14, a predetermined amount of the enzyme—for example, one of the enzymes listed hereinabove—is added to the mixture. For example, the pH value of the mixture is adjusted to a neutral or alkaline value using sodium hydroxide (NaOH) or a phosphate buffer. The mixture is then incubated at a predetermined incubation temperature for a predetermined incubation time interval—16. The enzyme specific values such as pH value, temperature, amount, incubation temperature and incubation time are determined based on common knowledge in the art and, furthermore, information made available by the supplier of the enzyme. The mixture can be agitated—18—during the incubation/hydrolysis by applying, for example, gentle shaking or stirring. Optionally, the adjustment of the pH value of the mixture is continued during a predetermined time interval at the beginning of the incubation/hydrolysis.

After elapse of the incubation time interval the hydrolysate is pasteurized—20—to inactivate the enzyme. A standard pasteurizing process can be employed, for example, in food production is used. Optionally, after pasteurizing, at least a portion of solid particles suspended in the hydrolysate is removed—22—using, for example, a suitable screening or filtering process known to one skilled in the art. Alternatively, the solid particles are left to settle at the bottom of a vessel containing the hydrolysate.

At 24, a predetermined amount of a plant or animal based oil that is liquid at the operational temperature of the centrifugation process—such as, for example, safflower oil—is added to the hydrolysate and, in one case, agitated for a predetermined time interval. The mixture of plant or animal based oil and hydrolysate is then centrifuged—26—producing layers of aqueous phase and oil phase. The mixture can then be centrifuged having an elevated temperature for enhancing the separation. For example, the mixture is centrifuged while still being hot from the previous pasteurizing process. At 28, the oil layer produced during the centrifuging is removed. The centrifuging and removal of the oil layer are performed, for example, in a batch process with the oil layer being removed after stopping the centrifuging process after elapse of a predetermined time interval. Alternatively, the oil layer is continuously removed during the centrifuging process which is typically applied in larger scale production processes.

The removed oil—sea cucumber oil diluted with the added plant or animal based oil—is then purified—30—using a standard process and standard technology employed, for example, in the fish oil production for purifying fish oil. Processes for purifying oil are, for example, washing and drying of the oil or bleaching and deodorizing of the oil. Optionally, an antioxidant such as, for example, a tocopherol is added to the oil to extend its shelf-life.

In one case, as illustrated in FIG. 1b, to increase the yield of the extracted oil a second predetermined amount of a plant or animal based oil is added to the hydrolysate left as the aqueous phase after the step 28 and the mixture is agitated for a predetermined time interval—32. The mixture of plant or animal based oil and hydrolysate is then centrifuged—34—followed by removing the oil layer—36—and purifying of the removed oil—38—using similar processing as in steps 26 to 30 hereinabove.

Figure 2A:
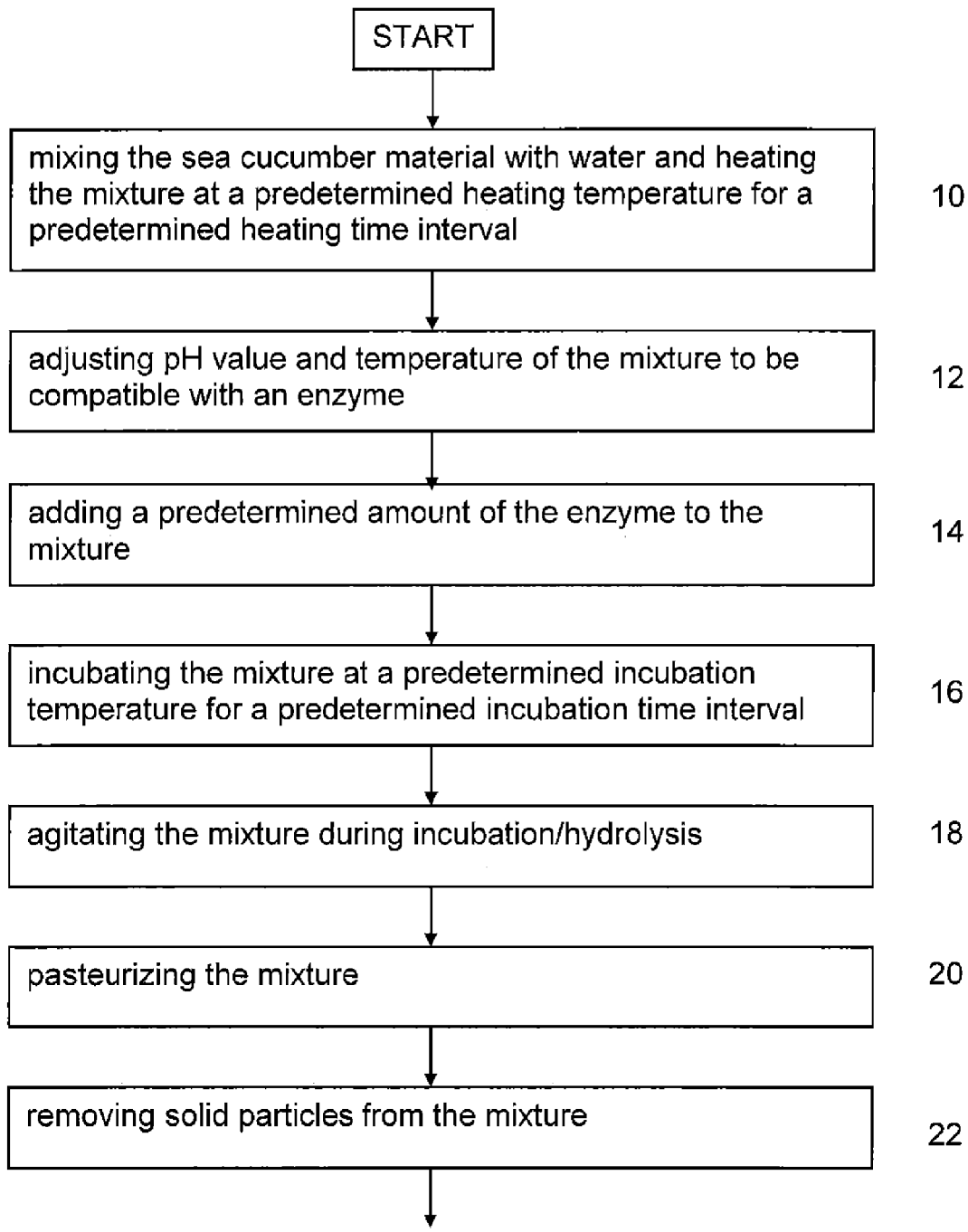
Figure 2A:
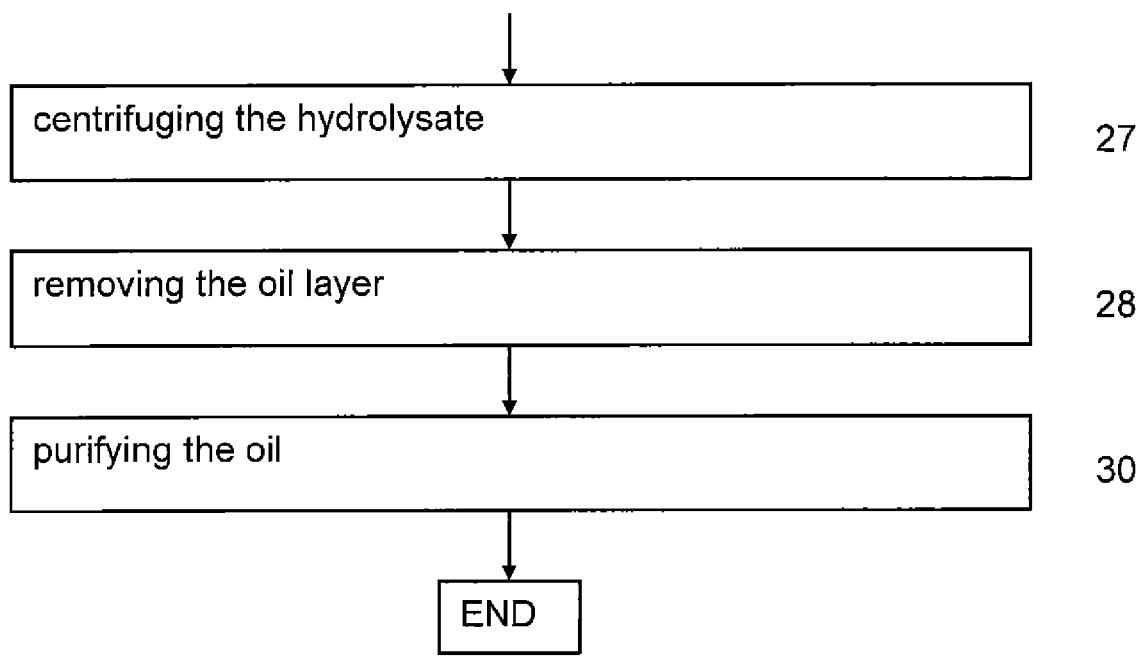

Optionally, as illustrated in FIG. 2a (same numbers indicate same processing steps as in FIG. 1a), the step of adding a plant or animal based oil to the hydrolysate is omitted and the same is centrifuged—27—after the step 22, followed by removing the oil layer—28—and purifying of the removed oil—30. This method provides substantially pure undiluted sea cucumber oil.

Figure 2B:
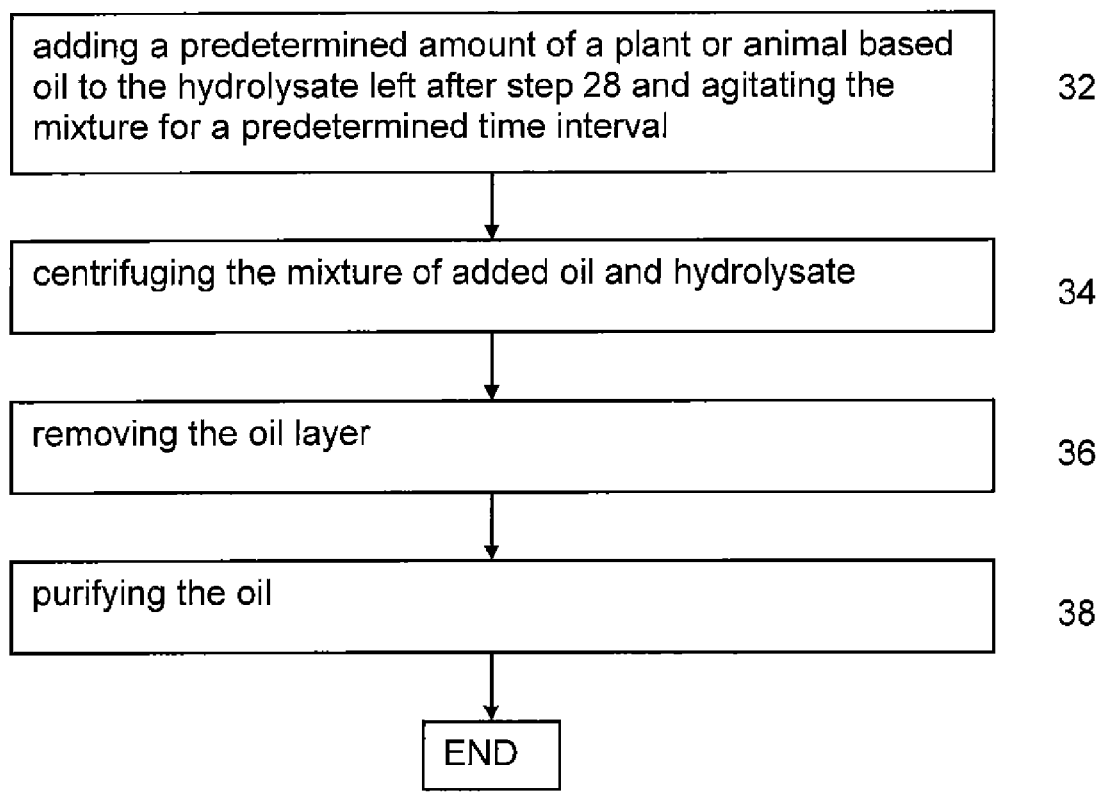

Further optionally, as illustrated in FIG. 2b, to increase the yield of the extracted oil a predetermined amount of a plant or animal based oil is added to the hydrolysate left as the aqueous phase after the step 27 and the mixture is agitated for a predetermined time interval—32. The mixture of plant or animal based oil and hydrolysate is then centrifuged—34—followed by removing the oil layer—36—and purifying of the removed oil—38—using similar processing as in steps 26 to 30 hereinabove.

In an example process described herein below, the above method, illustrated in FIGS. 1a and 1b, has been implemented on a laboratory scale. As is evident to one skilled in the art, the described process is implementable in larger scale manufacturing processes using standard chemical engineering and food processing technologies.

In step 10, 200 g sea cucumber viscera with a moisture content of approximately 80% is mixed with 80 g water and the mixture is then heated at approximately 90° C. for approximately 30 minutes.

In step 12, the pH value of the mixture is adjusted to an alkaline value of approximately 8.6 using NaOH and the temperature is adjusted to 58° C.-62° C.

In step 14, 450 mg of Genencore's Protex 40L enzyme (150,000 U/g) is added to the mixture.

In step 16, the mixture is incubated under gentle shaking or stirring at approximately 58° C.-62° C. for approximately 4 hours. During the first hour of the hydrolysis the pH value is adjusted to approximately 8.6 when necessary.

In step 20, the hydrolysate is pasteurized at approximately 90° C. for approximately 15 minutes to deactivate the enzyme.

In step 24, safflower oil is added to the hydrolysate at 10% weight of the sea cucumber viscera and the mixture is agitated at approximately 90° C. for approximately 10 minutes.

In step 26, the mixture—at approximately 90° C.—is centrifuged at g-force of approximately 4000 g.

In step 30, the removed oil is bleached and deodorized. Bleaching clay is added at 2% weight of the oil and the mixture is then heated to approximately 90° C. under medium vacuum (3 kPa to 100 mPa) for 30 minutes. The bleached oil is then heated to 160° C. for 2 hours. During both steps the oil is stirred and sparged with nitrogen.

In step 32, a second amount safflower oil is added to the hydrolysate left after step 28 at 10% weight of the sea cucumber viscera and the mixture is agitated at approximately 90° C. for approximately 10 minutes.

In step 34, the mixture—at approximately 90° C.—is centrifuged at g-force of approximately 4000 g.

In step 38, the removed oil is processed as in step 30.

The concentrations of sea cucumber oil in the oil removed after steps 26 and 34 have been determined—using spectrometric analysis—to be approximately 30% and 10%, respectively.

The present invention has been described herein with regard to certain embodiments. However, it will be obvious to persons skilled in the art that a number of variations and modifications can be made without departing from the scope of the invention as described herein.

What is claimed is:

1. A method for extracting oil from sea cucumber waste material comprising:
   mixing the sea cucumber waste material with water and heating the mixture at a predetermined heating temperature for a predetermined heating time interval;
   adjusting pH value and temperature of the mixture to be compatible with an enzyme;
   adding a predetermined amount of the enzyme to the mixture;
   incubating the mixture at a predetermined incubation temperature for a predetermined incubation time interval; and
   removing the oil from the mixture.

2. A method as defined in claim 1 comprising:
   pasteurizing the mixture;
   centrifuging the mixture producing an aqueous layer and an oil layer; and,
   removing the oil layer after centrifuging.

3. A method as defined in claim 2 comprising adding a predetermined amount of a plant or animal based oil to the mixture before centrifuging.

4. A method as defined in claim 3 wherein the plant or animal based oil comprises safflower oil.

5. A method as defined in claim 2 comprising:
   adding a predetermined amount of a plant or animal based oil to the aqueous phase;
   centrifuging the mixture of the plant or animal based oil and the aqueous phase; and,
   removing the oil layer after centrifuging.

6. A method as defined in claim 5 wherein the plant or animal based oil comprises safflower oil.

7. A method as defined in claim 1 comprising agitating the mixture during the incubation.

8. A method as defined in claim 2 comprising removing solid particles from the mixture before centrifuging the mixture.

9. A method as defined in claim 1 comprising purifying the removed oil.

10. A method as defined in claim 2 wherein the mixture is centrifuged while having a temperature proximate a pasteurizing temperature.

11. A method as defined in claim 1 wherein the sea cucumber waste material substantially comprises sea cucumber viscera.

12. A method as defined in claim 1 wherein the enzyme is one of a neutral and an alkaline protease.

13. A method as defined in claim 12 wherein the pH value is adjusted using sodium hydroxide (NaOH) or a phosphate buffer.

14. A method as defined in claim 1 comprising:
pasteurizing the mixture;
adding a first predetermined amount of a plant or animal based oil to the mixture;
centrifuging the mixture;
removing the oil layer after centrifuging;
adding a second predetermined amount of a plant or animal based oil to the remaining mixture;
centrifuging the remaining mixture; and,
removing the oil layer after centrifuging.

15. A compound comprising oil extracted from sea cucumber waste material using an enzyme.

16. A compound as defined in claim 15 comprising safflower oil.

17. A method for extracting oil from sea cucumber waste material comprising:
mixing the sea cucumber waste material with water and heating the mixture at a predetermined heating temperature for a predetermined heating time interval;
adjusting pH value and temperature of the mixture to be compatible with an enzyme;
adding a predetermined amount of the enzyme to the mixture;
incubating the mixture at a predetermined incubation temperature for a predetermined incubation time interval;
pasteurizing the mixture;
adding a predetermined amount of a plant or animal based oil to the mixture;
centrifuging the mixture; and,
removing the oil layer after centrifuging.

18. A method for extracting oil from sea cucumber waste material comprising:
mixing the sea cucumber waste material with water and heating the mixture at a predetermined heating temperature for a predetermined heating time interval;
adjusting pH value and temperature of the mixture to be compatible with an enzyme;
adding a predetermined amount of the enzyme to the mixture;
incubating the mixture at a predetermined incubation temperature for a predetermined incubation time interval;
pasteurizing the mixture;
adding a first predetermined amount of a plant or animal based oil to the mixture;
centrifuging the mixture;
removing the oil layer after centrifuging;
adding a second predetermined amount of a plant or animal based oil to the remaining mixture;
centrifuging the remaining mixture; and,
removing the oil layer after centrifuging.

* * * * *